United States Patent [19]

Kuroda et al.

[11] Patent Number: 4,985,174

[45] Date of Patent: Jan. 15, 1991

[54] RETICULOCYTE QUANTITATING REAGENT FOR FLOW CYTOMETRY

[75] Inventors: Tomoyuki Kuroda; Takahito Fukuhara, both of Hyogo, Japan

[73] Assignee: TOA Medical Electronics Co., Ltd., Kobe, Japan

[21] Appl. No.: 129,912

[22] Filed: Dec. 4, 1987

Related U.S. Application Data

[63] Continuation of Ser. No. 807,173, Dec. 9, 1985, abandoned.

[30] Foreign Application Priority Data

Jun. 6, 1985 [JP] Japan ................................. 60-123128

[51] Int. Cl.$^5$ ...................... G01N 21/64; G01N 31/02
[52] U.S. Cl. ................................................. 252/408.1
[58] Field of Search ..................................... 252/408.1

[56] References Cited

U.S. PATENT DOCUMENTS

| | | | |
|---|---|---|---|
| 3,371,310 | 2/1968 | Silverman | 367/21 |
| 3,866,161 | 2/1975 | Barr et al. | 367/21 |
| 3,883,247 | 5/1975 | Adams . | |
| 4,325,706 | 4/1982 | Gershman et al. | 23/230 B |
| 4,336,029 | 6/1982 | Natale | 23/230 B |
| 4,706,225 | 11/1987 | Raoult | 367/57 |
| 4,750,157 | 6/1988 | Shei | 367/45 |
| 4,883,867 | 11/1989 | Lee et al. | 536/28 |

FOREIGN PATENT DOCUMENTS

| | | |
|---|---|---|
| 789747 | 12/1980 | U.S.S.R. . |
| 939543 | 6/1982 | U.S.S.R. . |
| 2074340 | 10/1981 | United Kingdom . |

OTHER PUBLICATIONS

French Article—Medical Movement, A New Method of Counting Reticulocytes, La Presse Medicale, vol. 54, 17 Aout 1946.
Archives of Biochemistry and Biophysics, vol. 179, 1977, "Fluorescence of Free and Protein-Bound Auramine O", Raymond F. Chen, pp. 672-681.
Chem Abs. 19747m.
Sheriff; "Encyclopedic Dictionary of Exploration Geophysics," 1973, S. R. G., TN 269 SP4, p. 47.
Waters; "Reflection Seismology"; 1981, John Wiley & Sons, Inc., TN 269 W37; pp. 362 and 205.
Hutchinson, D.; "Surface-Consistant . . . and Statics"; 49th Europe Assn. Explor. Geophys. Artg., Belgrad Yugo; Abst. only.
Scharf et al., "Two Techniques of Inverse Filtering;" 3/82; Z. Angew Geol., vol. 28, #3, pp. 117-122; abst. only.
B. H. Sage, Jr. et al., Cytometry, 4, 222 (1983), "A Rapid Vital Staining Procedure for Flow Cytometric Analysis of Human Reticulocytes".
H. J. Tanke et al., Cytometry, 1, (5), 313, (1980), "Flow Cytometry of Human Reticulocytes Based on RNA Fluorescence".
H. J. Tanke et al., Blood, 61, (6), 1091 (1983), "Flow Cytometry of Reticulocytes Applied to Clinical Hematology".
G. Valet, Blut, 49, 83, (1984), "A New Method for Fast Blood Cell Counting and Partial Differentiation by Flow Cytometry".
J. W. Jacobberger, et al., Cytometry, 5, 589, (1984), "Flow Cytometric Analysis of Blood Cells Stained with the Cyanine Dye DiOC$_1$[3]: Reticulocyte Quantification".
P. N. Marshall, "Review: Reticulation, Polychromasia and Stippling of Erythrocytes", *Microscopica Acta*, vol. 81, No. 2, pp. 89-106, (Nov. 1978).

*Primary Examiner*—Robert L. Stoll
*Assistant Examiner*—Valerie Fee
*Attorney, Agent, or Firm*—Pearne, Gordon, McCoy & Granger

[57] ABSTRACT

Disclosed is a reagent containing auramine O for the fluorescent staining of reticulocytes in a sample of whole blood to permit quantitative determination of the reticulocytes by means of a flow cytometer.

8 Claims, 6 Drawing Sheets

Fig. 1(a) VISUAL OBSERVATION RET = 7.76%
MEASUREMENT 9.08%
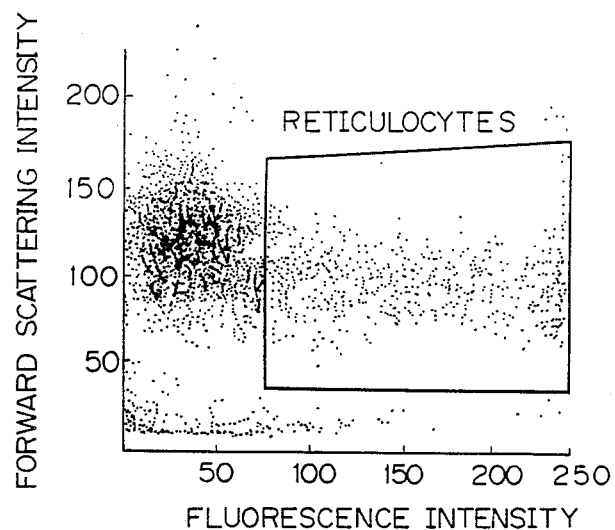
Fig. 1(b) VISUAL OBSERVATION RET = 0.53%
MEASUREMENT 0.48%
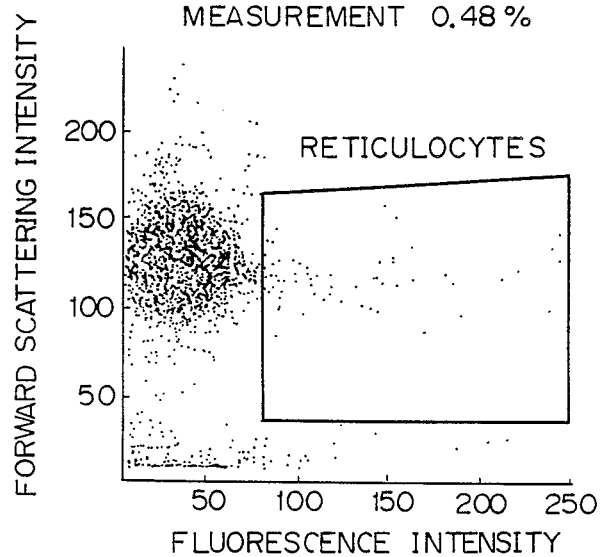

Fig. 3(a)  VISUAL OBSERVATION RET=1.20%
MEASUREMENT 1.23%
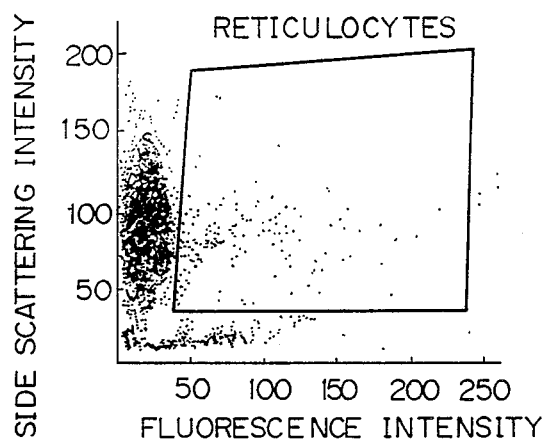
Fig. 3(b)  VISUAL OBSERVATION RET=6.50%
MEASUREMENT 6.80%
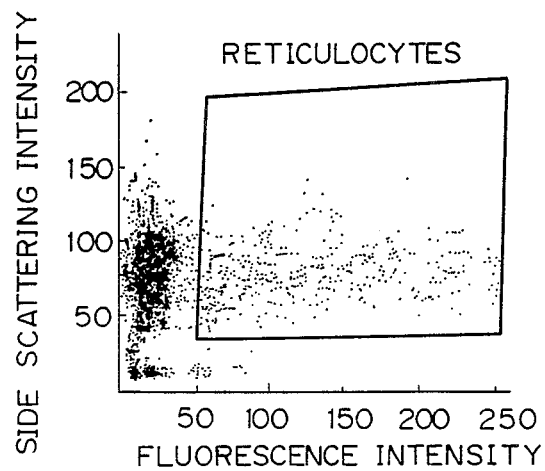

Fig. 4(a) VISUAL OBSERVATION RET = 1.20%
MEASUREMENT 1.14%
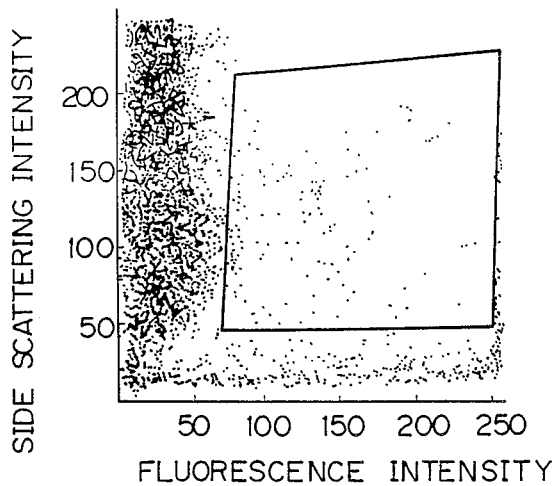
Fig. 4(b) VISUAL OBSERVATION RET = 6.50%
MEASUREMENT 6.22%
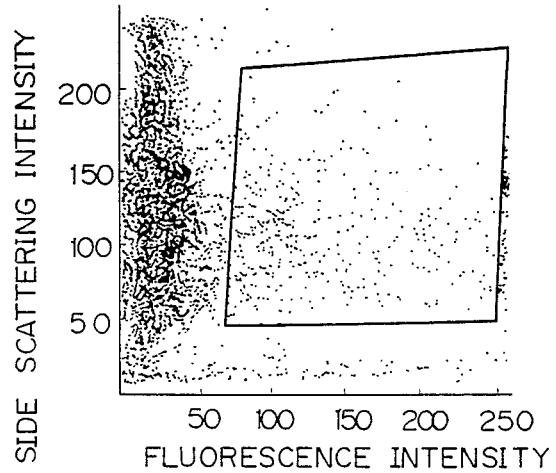

VISUAL OBSERVATION
RET = 1.0 %

MEASUREMENT 1.1%

VISUAL OBSERVATION
RET = 4.9 %

MEASUREMENT 5.5%

VISUAL OBSERVATION
RET = 12.5 %

MEASUREMENT 3.8%

RETICULOCYTE QUANTITATING REAGENT FOR FLOW CYTOMETRY

This is a continuation of application Ser. No. 06/807,173, filed on Dec. 9, 1985 now abandoned.

BACKGROUND OF THE INVENTION

This invention relates to a reagent for quantitating red blood cells, particularly mature erythrocytes and reticulocytes, adapted to use in the optical measurement of blood through flow cytometry.

Immature erythrocytes in a blood specimen are referred to as reticulocytes and ordinarily make up 0.7 to 2.2% of the total red blood cell population. Reticulocytes are of vital importance in modern clinical tests as their quantitative determination provides support in diagnosing acute internal hemorrhage, hemolytic anemia and aplastic anemia.

Smears stained with a basic dye such as new methylene blue or brilliant cresyl blue are used in quantitating reticulocytes as a percentage of total red blood cell content based on observation of the dyed reticulocytes under a microscope. However, staining with a dye of the aforementioned type requires considerable time and labor with regard to pretreatment of the blood specimen and visual enumeration of the reticulocytes after they are stained. For these reasons, such method is unsuitable for cases where a large number of tests are to be performed. Accordingly, a blood test using flow cytometry has been developed and is finding success in raising the speed and accuracy of measurement. However, various problems still remain as far as the quantitating of reticulocytes is concerned.

Examples of the prior art include the teachings of U.S. Pat. Nos. 4,336,029, 4,325,706 and 4,284,412, which propose the use of acridine orange for staining reticulocytes. Acridine orange produces red fluorescence upon being adsorbed by the reticulocyte RNA component and makes quantitative determination of the reticulocytes possible by allowing the red fluorescence to be distinguished from the green fluorescence produced by mature erythrocytes, which constitute the majority of the red blood cell population. However, the use of acridine orange is accompanied by the following problems: (A) The dye solution itself exhibits strong background fluorescence, which appears as background noise when measuring the intensity of fluorescence originating from the blood cells. The result is the likelihood of measurement error. (B) Since the fluorescence is beyond the red region of 630 nm, a highly sensitive fluorometric apparatus is required. (C) Since non-specific staining proceeds to be high degree and red fluorescence is produced in the mature erythrocytes, it is difficult to prepare a dye composition with little error from one blood sample to another. (D) The platelets are stained strongly and both the platelets and red blood cells are passed through a counting aperture in the flow cytometer simultaneously during measurement. When this is done, the intensity of light scattered by the mature erythrocytes and the intensity of red fluorescence from the platelets are measured at the same time. This constitutes the reticulocyte signal level and, hence, is a source of error. (E) The acridine orange solution is strongly dependent upon the environment, so that the intensity of fluorescence tends to vary.

The specification of Japanese Patent Application Laid-Open No. 59-142465 discloses use of thioflavine T as the dye. Following RNA staining a blood specimen using the proposed dye, background fluorescence and non-specific fluorescence of mature red blood cells are reduced by dilution and washing, after which reticulocyte RNA fluorescence is sensed and measured by a flow cytometer. The disadvantages of this approach are as follows: (F) Specific fluorescence caused by the dye for RNA bonding is also reduced with the reduction in non-specific fluorescence through dilution. This demands use of photometric equipment which is highly sensitive to fluorescence. (G) Since the decline in the intensity of fluorescence with time is quite sudden after dilution, data having a high degree of reproducibility cannot be obtained. (G') Dyeing requires a comparatively long period of time.

Pyronine Y is also used as a dye. Fixed red blood cells are washed after RNA staining to completely remove nonspecific fluorescence and background fluorescence, after which specific fluorescence caused by the dye for RNA bonding is measured. Here the drawbacks are: (H) The process steps of fixing the blood cells in advance, staining and washing are time consuming and require much more time than other methods. As a result, this approach is not suitable for dealing with a large number of samples. (I) Pyronine Y itself has a very low fluorescence quantum efficiency and, hence, measurement is possible only with excitation using a laser source having a large output. (J) Since pyronine Y will form bonds only with RNA and DNA of a low polymerization degree, the efficiency of RNA staining for obtaining specific fluorescence is poor.

SUMMARY OF THE INVENTION

The object of the present invention is to solve the aforementioned problems encountered in the conventional quantitative determination of reticulocytes by flow cytometry. Specifically, the invention seeks to employ a reagent containing a dye which eliminates the problems (A) through (E) related to the use of acridine orange, problems (F) through (G') ascribable to use of thioflavine T and problems (H) through (J) caused by using pyronine Y, and to intensify the strength of reticulocyte fluorescence in a stained sample while at the same time reducing the background fluorescence of the sample solution in order to raise the S/N ratio when fluorescence is measured, the ultimate objective being to effect a major improvement in reticulocyte quantitation.

According to the present invention, the foregoing object is attained by a reagent containing auramine O for the fluorescent staining of reticulocytes in a sample of whole blood to permit quantitative determination of the reticulocytes by means of a flow cytometer.

BRIEF DESCRIPTION OF THE DRAWINGS

FIGS. 1(a) and 1(b) show histograms in which the intensity of red fluorescence is plotted against the intensity of forward scattered light by flow cytometry using the reagent of the present invention;

FIGS. 3(a), 3(b) and 4(a), 4(b) are histograms similar to those of FIGS. 1(a), 1(b) but illustrative of different embodiments of the present invention;

DETAILED DESCRIPTION

Figure 2:
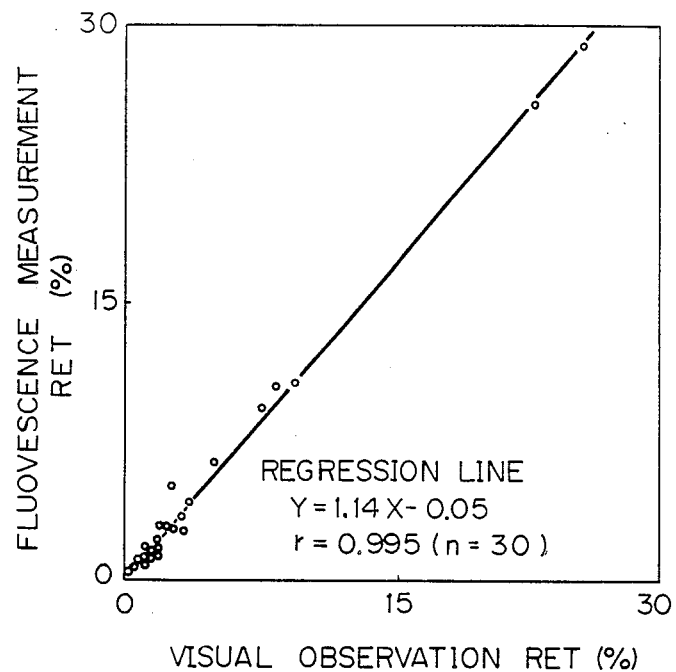
FIG. 2 is a graph based on FIGS. 1(a), 1(b) showing a correlation between measurement data indicative of reticulocyte quantitation according to the present invention and data indicative of reticulocyte quantitation according to conventional microscopy.

The red blood cells in a specimen of whole blood include mature red blood cells, namely the erythrocytes, and the young red blood cells, or reticulocytes, which have a high RNA content. According to the present invention, the erythrocytes and reticulocytes are made distinguishable from each other with a high degree of precision by subjecting the reticulocytes to fluorescent staining that results in strong and vivid fluorescence without influencing the percentage of reticulocytes or the red blood cell concentration. To this end, the present invention provides a reagent characterized by use of auramine for the fluorescent staining of reticulocytes to enable their quantitation by fluorescence using flow cytometry. Preferably, in order to stabilize the shape of the blood cells, an alkaline metal salt such as sodium chloride is added to render the dye solution isotonic. Also, a buffer may be added to raise the blood cell staining efficiency.

Auramine O, which can be used as the fluorescence stain, is of the formula

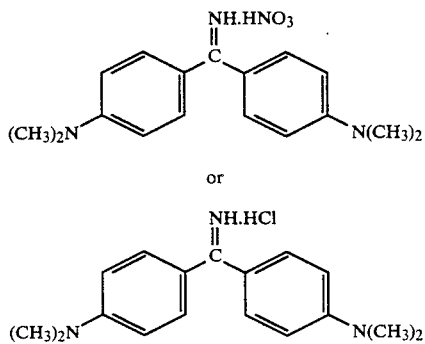

Auramine G can also be used, the formula being

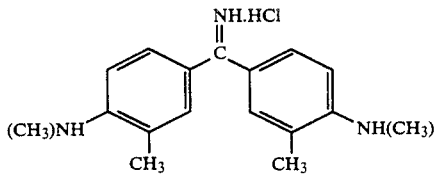

Another auramine which can be used is bis-(4-N,N-diethylaminophenol) imino methane, having the following formula, manufactured from diethylaniline or the like:

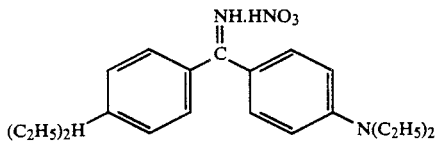

These auramines provide the stained blood cells with a vivid hue and they themselves possess a strong staining property.

When an auramine is employed as the fluorescent stain, adding a trace amount of a surfactant such as triton-X enables uniformalization of the stained mature erythrocytes and reticulocytes to be achieved efficiently and promotes an increase in the intensity of scattered light and fluorescence from each blood cell. This latter effect can be enhanced by addition of glutaraldehyde. The end result is to attain a relative reduction in the background fluorescence of the solution. Accordingly, a consolidated reticulocyte distribution can be obtained and membrane viscosity reduced to achieve a highly discriminative enumeration of the reticulocytes. This contributes to a quantitative determination of improved accuracy.

Preferably, the amount of auramine contained is 20 to 2500 micrograms per milliliter of the reagent, and the amount of alkali metal salt, such as sodium chloride, is 5 to 20 milligrams per milliliter of the reagent. The pH is adjusted to from 6 to 10.

An isotonic, buffered stain solution containing the above-described ingredients constitutes a reagent for quantitating blood cells, particularly reticulocytes, and is for being mixed with a whole blood sample treated with EDTA or the like to prevent coagulation.

When a blood cell quantitating reagent of the foregoing composition is mixed with a sample of whole blood treated with anticoagulant, the auramine dye vividly stains all blood cells inclusive of reticulocytes and, in particular, separates out upon forming bonds with the RNA contained in the blood cells and takes on yellow fluorescence no less than one hour later. The stained blood cells are subjected to an excitation light source of a wavelength such as that of a mercury or xenon arc lamp or a laser (He-Cd laser or Ar laser), and a flow cytometer is used to detect yellow fluorescence of about 520–700 nm or more.

Using the reagent of the present invention makes it possible to readily and clearly distinguish mature erythrocyte groupings from immature reticulocytes and, moreover, from platelet groupings.

EXAMPLE 1

A reagent according to the present invention was prepared by adding 0.01 M/l of a phosphate buffer solution and water to 1 g of auramine 0 and 9 g of sodium chloride to form 1l of solution. The pH was adjusted to 7.20. Added to 5 ml of the resulting reagent was 10 μl of EDTA-treated fresh cow blood. After incubating for 10 minutes at room temperature, the mixture was introduced into a fluorescence flow cytometer. The light source used was a mercury arc lamp generating an excitation light beam of up to about 480 nm. Fluorescence in excess of 520 nm was detected. FIGS. 1(a), 1(b) and FIG. 2 show the results of measurement for 30 samples of 0.1–26% reticulocytes in which the group of reticulocytes detected by forward scattering-backward fluorescence is enclosed by the rectangle. FIG. 2 shows excellent correlation between the measured data (plotted along the Y axis) and the data based on visual enumeration of the reticulocytes (plotted along the X axis). The correlation coefficient r obtained 0.995. The regression line Y was 1.14× −0.05.

EXAMPLE 2

Side-scattered light, with which it is comparatively difficult to distinguish between red blood cell groupings and platelets since this does not readily give an indication of cell volume, was measured together with backward fluorescence, and mature erythrocytes, reticulocytes and platelets were individually enumerated.

A reagent according to the present invention was prepared by adding 0.02 M/l of a phosphate buffer solution and water to 400 mg of auramine O, 9 g of sodium chloride and 30 mg of glutaric aldehyde to form 1 l of solution. The pH was adjusted to 8.00. The reagent obtained exhibited a yellow color. Added to 5 ml of the reagent was 10 μl of EDTA-treated blood or a specimen in which reticulocytes were concentrated from the blood by a density gradient method. After incubating for 10 minutes at room temperature, the mixture was subjected to a fluorescence flow cytometer, as set forth in Example 1, where fluorescence in excess of 580 nm and sidewardly-scattered light were detected and measured. The correlation with the visually obtained data was excellent from low to high values of reticulocyte percentage, and the light scattered by the red blood cells was comparatively uniform. The results are as shown in FIGS. 3(a), 3(b).

EXAMPLE 3

Reticulocytes were quantitated by side scattering-/backward fluorescence using specimens similar to that of Example 2 but by lowering the auramine concentration by at least one place and varying the numerical values of the composition.

A reagent according to the present invention was prepared by adding 0.02 M/l of a borate buffer solution and water to 30 mg of auramine O, 13 g of sodium chloride and 100 mg of glutaricaldehyde to form 1 l of solution. The pH was adjusted to 9.00. The reagent obtained exhibited a yellow color. Added to 5 ml of the reagent was 10 μl of a specimen in which reticulocytes were concentrated from EDTA-treated blood by the density gradient method. After incubating for 10 minutes at room temperature, the mixture was subjected to a flow cytometer for quantitation of the blood cells. The results are as shown in FIGS. 4(a), 4(b). It will be appreciated that though there is some spreading of the scattering produced by the blood cells, the measured values remain almost unchanged.

EXAMPLE 4

A reagent according to the present invention was prepared by adding 0.01 M/l of a phosphate buffer solution and water to 400 mg of auramine O and 8 g of sodium chloride to form 1 l of solution of pH 8.00. Added to 2 ml of the resulting reagent was 10 μl of fresh cow blood containing the anticoagulant EDTA. After incubating for 30 seconds at room temperature, the mixture was introduced into a fluorescence flow cytometer. The light source used was an argon ion blue laser. The sample was excited at a low power of 10 mw and a wavelength of 488 nm, and forward scattered light and side fluorescence in excess of 520 nm were measured by means of a photomultiplier tube.

Despite this low power of excitation, which is unheard of in the prior art, for 30 samples a value of 0.97 was obtained as the coefficient r of correlation with the conventional visual method, and the regression line Y obtained was $1.145X - 0.007$ (%). Thus, the data obtained coincide with the visual data for low to high values of reticulocyte counts.

Figure 5A:
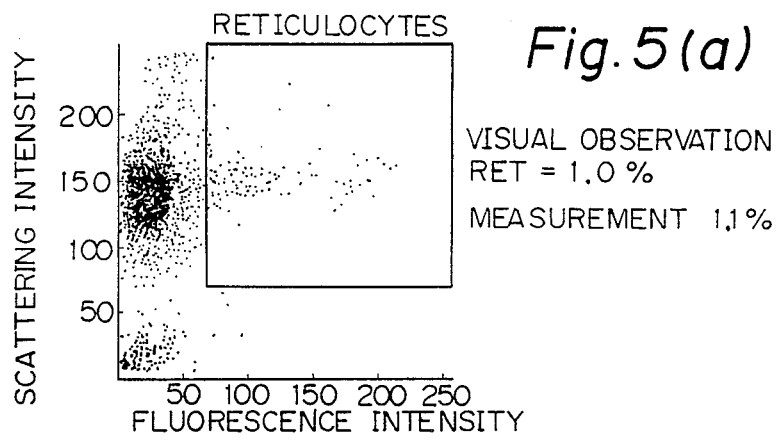
FIGS. 5(a), 5(b) and 5(c) are histograms similar to those of FIGS. 1, 3 and 4 but illustrative of further embodiments of the present invention.
Figure 5B:
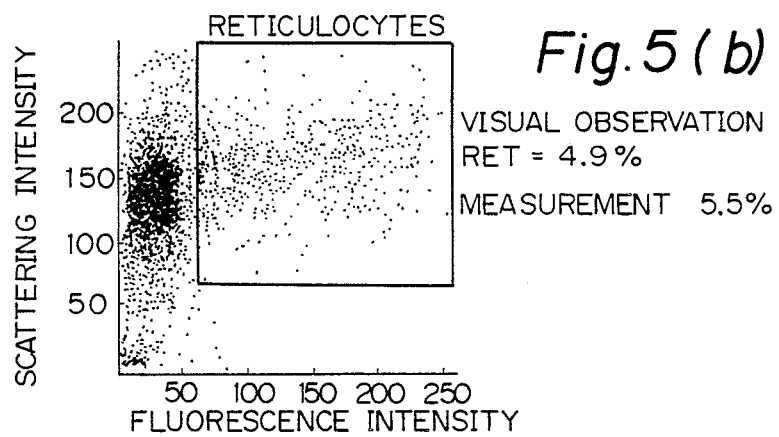
Figure 5C:
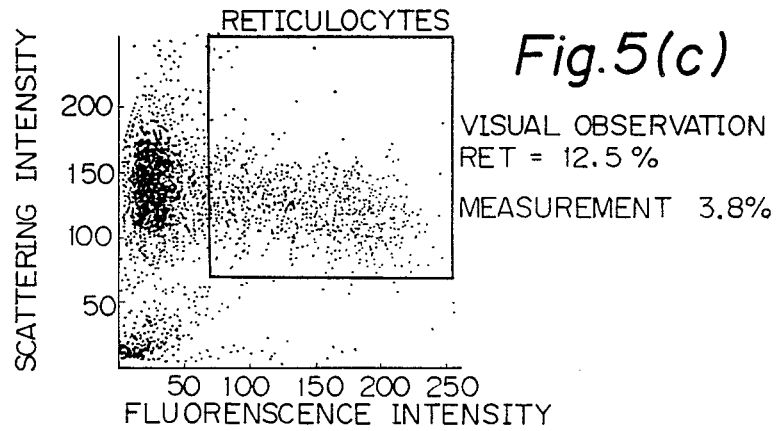

FIGS. 5(a), (b), (c) are histograms in which the intensity of fluorescence is plotted along the horizontal axis and the intensity of scattered light is plotted along the vertical axis, with each point on the histogram representing a cell. The numerical values to the right of the histograms indicate the measured and visually observed values of the number of reticulocytes enclosed by the square.

Figure 6:
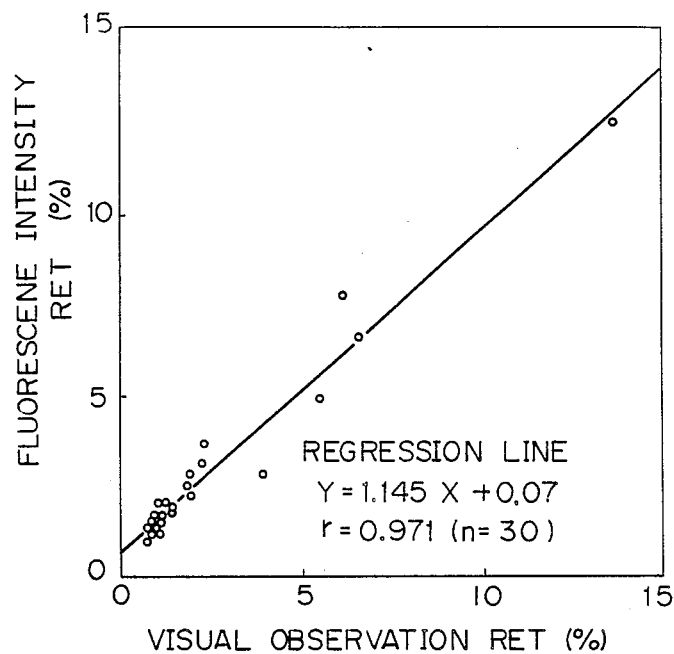
FIG. 6 is a graph of a correlation similar to that of FIG. 2 but associated with FIG. 5.

FIG. 6 is a graph representing the above-mentioned correlation. Measured values obtained using auramine O are plotted along the horizontal axis, and values based on the visual method are plotted along the vertical axis.

Thus, when the reagent of the present invention is mixed with a blood sample are passed through a flow cytometer, not only can red blood cell groupings be clearly differentiated from platelets, but the distinction between mature, ordinary erythrocytes and immature reticulocytes contained in the red blood cell groupings is made perfectly clear in the form of vivid staining. Excellent correlation with measurement data based on visual observation has been verified. Furthermore, since background fluorescence of the solution following mixing with a blood sample can be greatly reduced, the entirety of the fluorescence attributed to the blood cells can be picked up specifically. This is in contradistinction to the conventional method using acridine orange, where some of the fluorescence is picked up selectively through use of a filter. The present invention also makes it possible to conduct measurement using a low-power excitation light source. In such case, even if the auramine used as the dye is adsorbed non-selectively by a membrane of mature erythrocytes, the fluorescence produced is of very weak intensity. The fluorescence ascribable to the reticulocytes, on the other hand, is high in intensity and readily distinguished. In addition, staining is rapid, allowing the satisfactory staining of samples having large numbers of reticulocytes in less than one-tenth the time needed for staining with acridine orange. According to flow cytometry, the sample solution in which blood cells are suspended is passed through a counting aperture, at which time the platelets and mature erythrocytes pass through the aperture simultaneously. When this occurs, an error is the result since the mature erythrocytes are counted as reticulocytes. When the reagent of the present invention is used, however, the intensity of reticulocyte fluorescence is raised to an extremely high level, enabling the mature erythrocytes and reticulocytes to be enumerated accurately without the erythrocyte and reticulocyte counts being confused. In this connection, if the auramine concentration is raised a certain degree, aggregation and simultaneous passage of these blood cells is prevented owing to the repulsion of the non-specifically adsorbed dye on the cells.

Since auramine is readily broken down by raising pH, cleansing of the flow cytometer flow passages is a simple matter even if the auramine attaches itself thereto. Further, when auramine is used, the distribution of forward scattering intensity of the red blood cells appears in more coherent or consolidated form owing to the characteristics of the dye itself, so that the wide dispersal heretofore obtained in the prior art is reduced. This facilitates the separation of platelets and red blood cells by forward scattering and enables the two to be counted more accurately. Further, even though non-specific staining conditions are increased with use of auramine, this leads to stronger specific staining which increases the intensity of reticulocyte fluorescence while not increasing the intensity of mature erythrocyte fluorescence. As a result, the degree of staining may be raised to profoundly enhance the sensitivity of the flow cytometer to fluorescence, and the adaptability of the flow cytometer to samples having a low percentage of reticulocytes can be improved while maintaining the accuracy at which the reticulocytes are enumerated.

What is claimed is:

1. A method for quantitating reticulocytes in a fresh blood sample stained with auramine O by flow cytometry comprising the steps of:
   (a) fluorescent staining RNA in blood cells of the fresh blood sample for a period of about ten minutes with a composition of auramine O, said composition containing 20 to 2500 μg/ml of auramine O, alkaline metal salt in an amount sufficient to stabilize the shape of the blood cells, and buffer to maintain the pH of the composition at a value in the range of 6 to 10;
   (b) flowing said stained cells through a detecting area of a flow cytometer having a light source with a suitable excitation wavelength;
   (c) detecting scattered light and fluorescence above 520 nm emitted from cells;
   (d) distinguishing platelets from cells by said detected scattered light;
   (e) discriminating mature erythrocytes, reticulocytes, and leucocytes by RNA content using auramine O fluorescence; and
   (f) calculating the ratio of reticulocytes to the total erythrocytes and/or relative RNA content in a unit volume of fresh blood and/or relative RNA content in a unit volume of fresh blood.

2. A method as described in claim 1, wherein said light sources is an argon ion laser of 488 nm, and said scattered light is a forward scattered light.

3. A method as described in claim 1, wherein said light source is a mercury arc lamp, and said scattered light is a forward scattered light.

4. A method as described in claim 1, wherein said light source is a mercury arc lamp, and said scattered light is a side scattered light.

5. A method for quantitating reticulocytes in a fresh blood sample stained with auramine O by flow cytometry comprising the steps of:
   (a) fluorescent staining RNA in blood cells of the fresh blood sample for a period of about thirty seconds with a composition of auramine O, said composition containing 20 to 2500 μg/ml of auramine O, alkaline metal salt in an amount sufficient to stabilize the shape of the blood cells, and buffer to maintain the pH of the composition at a value in the range of 6 to 10;
   (b) flowing said stained cells through a detecting area of a flow cytometer having a light source with a suitable excitation wavelength;
   (c) detecting scattered light and fluorescence above 520 nm emitted from cells;
   (d) distinguishing platelets from cells by said detected scattered light;
   (e) discriminating mature erythrocytes, reticulocytes and leucocytes by RNA content using auramine O fluorescence; and
   (f) calculating the ratio of reticulocytes to the total erythrocytes and/or the numbers of reticulocytes in a unit volume of fresh blood and/or relative RNA content in a unit volume of fresh blood.

6. A method for quantitating reticulocytes in a fresh blood sample stained with auramine O by flow cytometry without the use of a chelating reagent or an amino-group reacting reagent, comprising the steps of:
   (a) fluorescent staining RNA in blood cells of the fresh blood sample with a composition consisting essentially of 20 to 2500 μg/ml of auramine O, alkaline metal salt in an amount sufficient to stabilize the shape of the blood cells, water, and buffer to maintain the pH of the composition at a value in the range of 6 to 10;
   (b) flowing said stained cells through a detecting area of a flow cytometer having a light source with a suitable excitation wavelength;
   (c) detecting scattered light and fluorescence above 520 nm emitted from cells;
   (d) distinguishing platelets from cells by said detected scattered light;
   (e) discriminating mature erythrocytes, reticulocytes and leucocytes by RNA content using auramine O fluorescence; and
   (f) calculating the ratio of reticulocytes to the total erythrocytes and/or the numbers of reticulocytes in a unit volume of fresh blood and/or relative RNA content in a unit volume of fresh blood.

7. A method according to claim 6, wherein said sample and composition are contacted for a period of time equal to about ten minutes in step (a) to effect staining.

8. A method according to claim 6, wherein said sample and composition are contacted for a period of time equal to about thirty seconds in step (a) to effect staining.

* * * * *